(12) United States Patent
Paik

(10) Patent No.: US 10,245,089 B2
(45) Date of Patent: Apr. 2, 2019

(54) FIXING TOOL FOR OPEN-WEDGE HIGH TIBIAL OSTEOTOMY

(71) Applicant: Hae Sun Paik, Seoul (KR)

(72) Inventor: Hae Sun Paik, Seoul (KR)

(*) Notice: Subject to any disclaimer, the term of this patent is extended or adjusted under 35 U.S.C. 154(b) by 238 days.

(21) Appl. No.: 15/303,515

(22) PCT Filed: May 7, 2014

(86) PCT No.: PCT/KR2014/004035
§ 371 (c)(1),
(2) Date: Oct. 11, 2016

(87) PCT Pub. No.: WO2015/160021
PCT Pub. Date: Oct. 22, 2015

(65) Prior Publication Data
US 2017/0035479 A1 Feb. 9, 2017

(30) Foreign Application Priority Data
Apr. 18, 2014 (KR) .................. 10-2014-0046871

(51) Int. Cl.
A61B 17/80 (2006.01)
A61B 17/82 (2006.01)
A61B 17/86 (2006.01)

(52) U.S. Cl.
CPC .......... *A61B 17/8095* (2013.01); *A61B 17/80* (2013.01); *A61B 17/8004* (2013.01);
(Continued)

(58) Field of Classification Search
CPC ...................................... A61B 17/80–17/8095
See application file for complete search history.

(56) References Cited

U.S. PATENT DOCUMENTS 7,108,697 B2 * 9/2006 Mingozzi ........... A61B 17/8095
606/286
8,246,660 B2 * 8/2012 Boris ................... A61B 17/808
606/246
(Continued)

FOREIGN PATENT DOCUMENTS

CN 1832706 A 9/2006
EP 1308135 A2 5/2003
(Continued)

OTHER PUBLICATIONS

Extended European Search Report for EP Application No. 14889634.3 dated Nov. 27, 2017.
(Continued)

*Primary Examiner* — Zade Coley
(74) *Attorney, Agent, or Firm* — STIP Law Group, LLC

(57) ABSTRACT

The present invention relates to a fixing tool for an open-wedge high tibial osteotomy, and a fixing tool for an open-wedge high tibial osteotomy, which is installed on a tibia cut open due to a tibial osteotomy, includes: a fixing plate which includes a head portion that has a plurality of nut holes, and an elongated plate that has a plurality of nut holes and a long hole and is formed to protrude from one side of the head portion; screws which are coupled to the nut holes; and a block which is detachably installed in the long hole by using a fixing screw. Therefore, the fixing tool is closely fixed to a tibia, which has been cut open due to a procedure of a high tibial osteotomy, thereby enabling solid union of the tibia.

18 Claims, 12 Drawing Sheets

(52) U.S. Cl.
CPC .......... *A61B 17/8061* (2013.01); *A61B 17/82* (2013.01); *A61B 17/86* (2013.01)

(56) References Cited

U.S. PATENT DOCUMENTS

| | | | | |
|---|---|---|---|---|
| 2003/0199875 A1* | 10/2003 | Mingozzi | ........... | A61B 17/8095 606/297 |
| 2004/0172028 A1* | 9/2004 | Roger | ............... | A61B 17/8095 606/71 |
| 2005/0015089 A1* | 1/2005 | Young | ............... | A61B 17/8014 606/915 |
| 2005/0251138 A1* | 11/2005 | Boris | ............... | A61B 17/7071 623/17.11 |
| 2006/0004362 A1* | 1/2006 | Patterson | ........... | A61B 17/8057 606/291 |
| 2008/0195099 A1 | 8/2008 | Minas | | |
| 2009/0177203 A1* | 7/2009 | Reiley | ............... | A61B 17/8095 606/87 |
| 2010/0016858 A1* | 1/2010 | Michel | ............... | A61B 17/8057 606/70 |
| 2010/0241173 A1* | 9/2010 | Orbay | ............... | A61B 17/8057 606/286 |
| 2012/0184959 A1* | 7/2012 | Price | ................... | A61B 17/8009 606/70 |
| 2013/0138154 A1* | 5/2013 | Reiley | ................ | A61B 17/8095 606/280 |
| 2014/0039498 A1 | 2/2014 | Chatain et al. | | |

FOREIGN PATENT DOCUMENTS

| | | | |
|---|---|---|---|
| EP | 2510893 | A1 | 10/2012 |
| FR | 2 785 519 | A1 | 5/2000 |
| FR | 2785519 | A1 * 5/2000 ........... A61B 17/151 |
| JP | 2007-500069 | A | 1/2007 |
| JP | 2010-220762 | A | 10/2010 |
| JP | 2011-010792 | A | 1/2011 |
| KR | 10-2006-0035604 | A | 4/2006 |
| KR | 10-0884491 | B1 | 2/2009 |
| KR | 10-1253915 | B1 | 4/2013 |
| KR | 10-1342493 | B1 | 12/2013 |
| WO | WO 01/56452 | A2 | 8/2001 |
| WO | WO 2007/100513 | A2 | 9/2007 |

OTHER PUBLICATIONS

International Search Report for International Patent Application No. PCT/KR2014/004035 filed May 7, 2014.

* cited by examiner d = 6 mm d = 11 mm d = 16 mm

FIXING TOOL FOR OPEN-WEDGE HIGH TIBIAL OSTEOTOMY

CROSS-REFERENCE TO RELATED APPLICATIONS

The present specification is a U.S. National Stage of International Patent Application No. PCT/KR2014/004035 filed May 7, 2014, which claims priority to and the benefit of Korean Patent Application No. 10-2014-0046871 filed in the Korean Intellectual Property Office on Apr. 18, 2014, the entire contents of which are incorporated herein by reference.

TECHNICAL FIELD

The present invention relates to a fixing tool for an open-wedge high tibial osteotomy. More particularly, the present invention relates to a fixing tool for an open-wedge high tibial osteotomy, which is fixed to a tibia, which has been cut open after an interior high tibial osteotomy, so as to enable solid union of the tibia.

BACKGROUND ART

Osteoarthritis causes angular deformity, which results from severe breakdown of joint cartilage of an inner knee joint, and results in pain, and when a patient stands or walks, progression of arthritis and pain become more severe because a body weight is concentrated to one side.

For performing a procedure for inward angular deformity, a method is used which performs an osteotomy on an inner proximal tibia in the vicinity of a knee, and then fixes the tibia by using a metallic plate.

The high tibial osteotomy is performed on a patient who is overweight and suffers from osteoarthritis of the knee. That is, the high tibial osteotomy is a method of performing an osteotomy on a proximal portion of the tibia so as to reduce pain by dispersing a load of the body weight, which is concentrated to an interior of a knee joint, further outward.

As illustrated in FIG. 1, assuming that a line, which connects a center of a coxa and a center of an ankle, is an axis of a lower limb, the line means a weight-bearing line while walking, and in a normal situation, the line runs through a center of the knee.

Therefore, the high tibial osteotomy refers to a procedure that allows the line to run through the center of the knee. Therefore, after the procedure, comparatively normal articulation motions, such as squatting and running, are enabled.

As the invention associated with the high tibial osteotomy, there is Korean Patent No. 10-1253915 (Apr. 5, 2013) "Connector for High Tibia Osteotomy".

Referring to FIG. 2, the connector for a high tibia osteotomy is characterized in that a through hole, through which a medical grade suture remaining after sewing a wound of a cartilage may pass, is formed in the form of a long hole.

However, because a main connecting body 10 of the disclosed connector for a high tibial osteotomy is formed in the form of a flat plate, there is a problem in that close contact force with an outer surface of the tibia deteriorates during a procedure of the high tibial osteotomy.

In addition, when fixing the main connecting body 10, screws 11 need to be coupled by using a separate tool to fix the main connecting body 10 or a practitioner needs to hold the main connecting body 10 to couple the screws 11, and as a result, there is difficulty in selecting a position of the main connecting body 10 and fixing the main connecting body 10.

Therefore, there is a problem in that a period of time required for the procedure is prolonged.

SUMMARY OF THE INVENTION

Technical Problem

Accordingly, the present invention has been made in an effort to solve the aforementioned problems, and an object of the present invention is to provide a fixing tool for an open-wedge high tibial osteotomy, which is fixed to a tibia, which has been cut open after an interior high tibial osteotomy, so as to enable solid union of the tibia.

In addition, another object of the present invention is to provide a fixing tool for an open-wedge high tibial osteotomy, which is closely fixed to the tibia, which has been cut open due to an open-wedge high tibial osteotomy, so as to facilitate a procedure and union of the tibia and support a load applied to the tibia.

Technical Solution

The aforementioned object is achieved by the present invention that provides a fixing tool for an open-wedge high tibial osteotomy, which is installed on a tibia cut open due to a tibial osteotomy, the fixing tool including: a fixing plate which includes a head portion that has a plurality of nut holes, and an elongated plate that has a plurality of nut holes and a long hole and is formed to protrude from one side of the head portion; screws which are coupled to the nut holes; and a block which is detachably installed in the long hole by using a fixing screw.

Here, the head portion may be curvedly formed at a predetermined curvature.

Further, the screws installed at both sides based on a center of the head portion may be installed to be inclined toward a center of the curvature.

In addition, tips of the screws, which are installed toward a centerline, that connects a center of the head portion and a center of the curvature, and installed at both sides based on the center of the head portion, may be installed to be spaced apart from the centerline.

In addition, the nut hole formed in the head portion may be inclinedly formed to have a gradient of 8 to 12 degrees in a direction toward the elongated plate.

In addition, the other side of the head portion may be inclinedly formed to have an inclination angle.

Here, the inclination angle may be 5 to 7 degrees.

In addition, a portion of the elongated plate connected with the head portion may be bent to have a bending angle.

Here, the bending angle may be 13 to 16 degrees.

In addition, a width of the elongated plate may be curvedly formed at a predetermined curvature.

Meanwhile, the block may include: an upper plate; and a pair of support protrusions which is formed from one side surface of the upper plate so as to be spaced apart from each other.

Here, the other side surface of the upper plate may be a curved surface having a predetermined curvature.

In addition, the support protrusions may include an upper support protrusion and a lower support protrusion, and at least one of the upper support protrusion and the lower support protrusion may protrude to be inclined in a width direction.

In addition, a ratio between a length of one side from the lower support protrusion to the upper support protrusion and a length of the other side may be 2:3.

In addition, the elongated plate may be curvedly formed in a width direction to have a predetermined curvature, and the curvature of the elongated plate and the curvature of the upper plate may be equal to each other.

In addition, the head portion may include at least two guide holes formed such that guide pins are installed in at least two guide holes.

Advantageous Effects

The fixing tool for an open-wedge high tibial osteotomy according to the exemplary embodiment of the present invention, which has the aforementioned configuration, is closely fixed to the tibia which has been cut open due to the high tibial osteotomy, thereby enabling solid union of the tibia.

That is, the fixing plate is curvedly formed at a predetermined curvature, and a portion of the fixing plate is bent and then closely attached to the tibia, thereby improving integrality with the tibia.

In addition, it is possible to support the cut-out portion of the tibia and maintain a rearward inclination angle of the tibia by using the block.

In addition, since the fixing tool for an open-wedge high tibial osteotomy is temporarily fixed by using a guide pin, it is possible to ensure convenience of a procedure of the open-wedge high tibial osteotomy.

DETAILED DESCRIPTION

Figure 1:
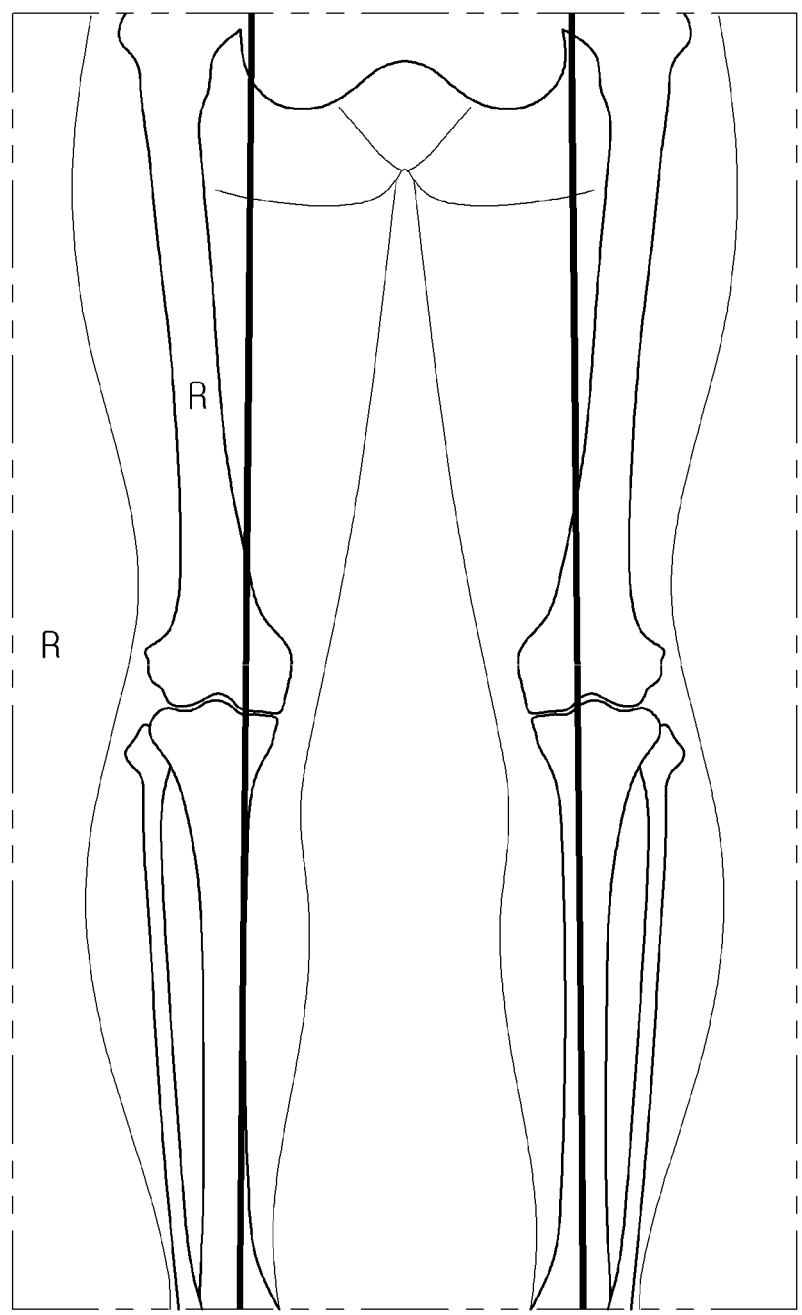
FIG. 1 is an X-ray photograph of a person required to be subjected to a procedure of a high tibial osteotomy.
Figure 2:
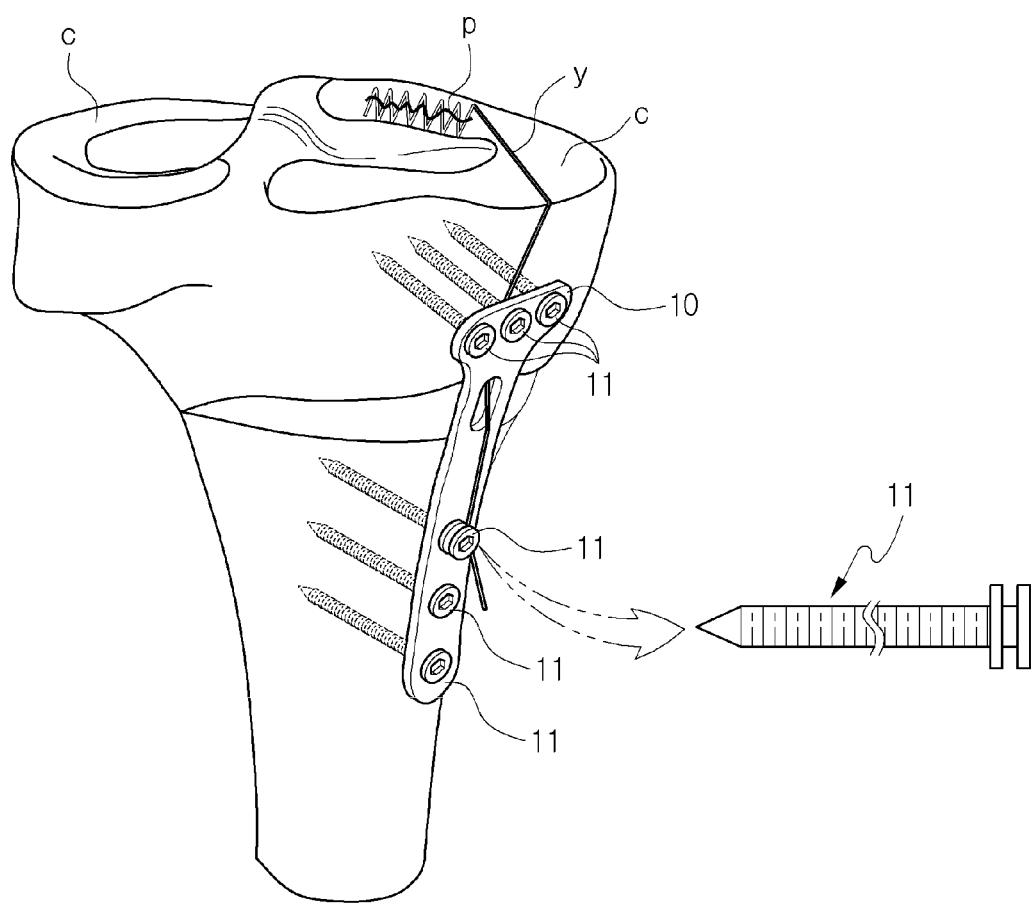
FIG. 2 is a view illustrating a connector for a high tibial osteotomy in the related art.

Hereinafter, exemplary embodiments of the present invention will be described in detail with reference to the accompanying drawings in order to clarify solutions for solving the technical problems of the present invention. However, in the description of the present invention, a detailed explanation of publicly known related technologies will be omitted in order to avoid unnecessarily obscuring the subject matter of the present invention. In addition, the following terms are defined considering the functions of the present invention and may vary depending on the intention or usual practice of a designer or a manufacturer. Therefore, the definitions thereof should be made based on the entire contents of the present specification. In addition, like drawing numerals (reference numerals) indicate like elements throughout the specification.

Hereinafter, a fixing tool for an open-wedge high tibial osteotomy according to an exemplary embodiment of the present invention will be described.

Figure 3:
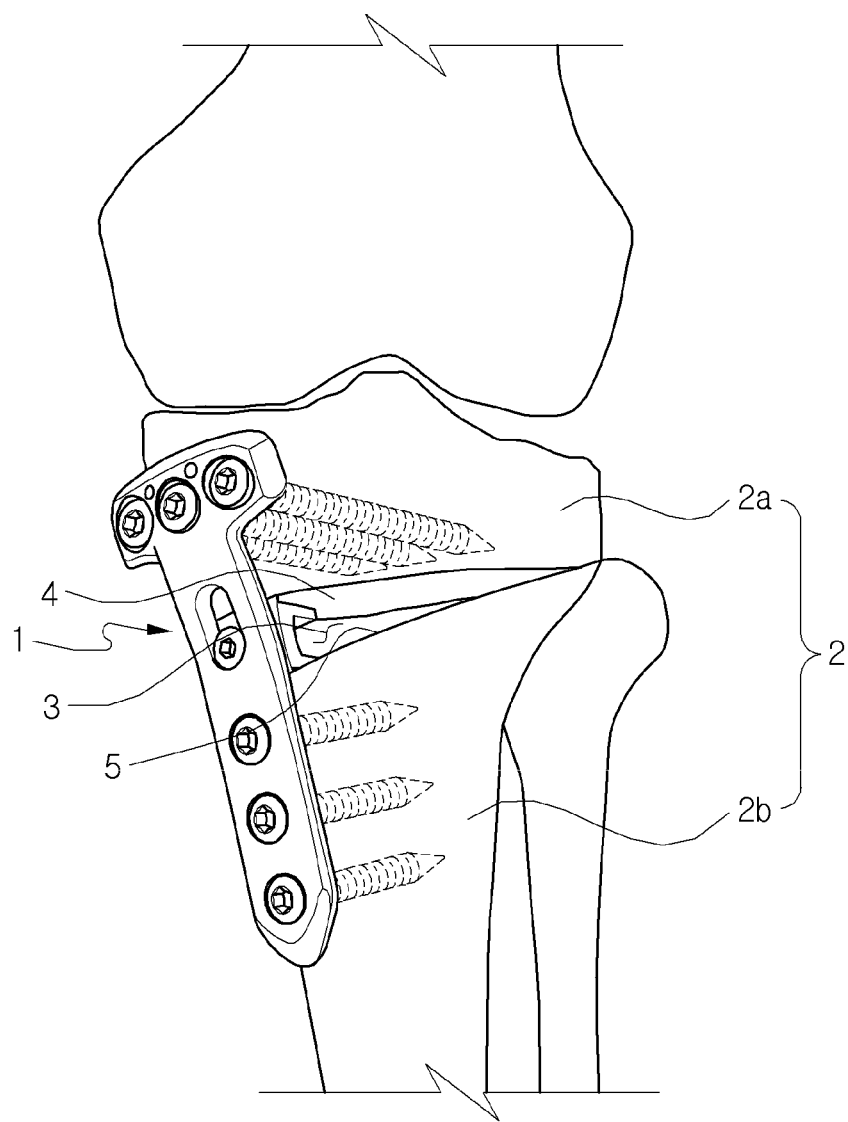
FIG. 3 is a view illustrating a state in which a fixing tool for an open-wedge high tibial osteotomy according to an exemplary embodiment of the present invention is used.
Figure 4:
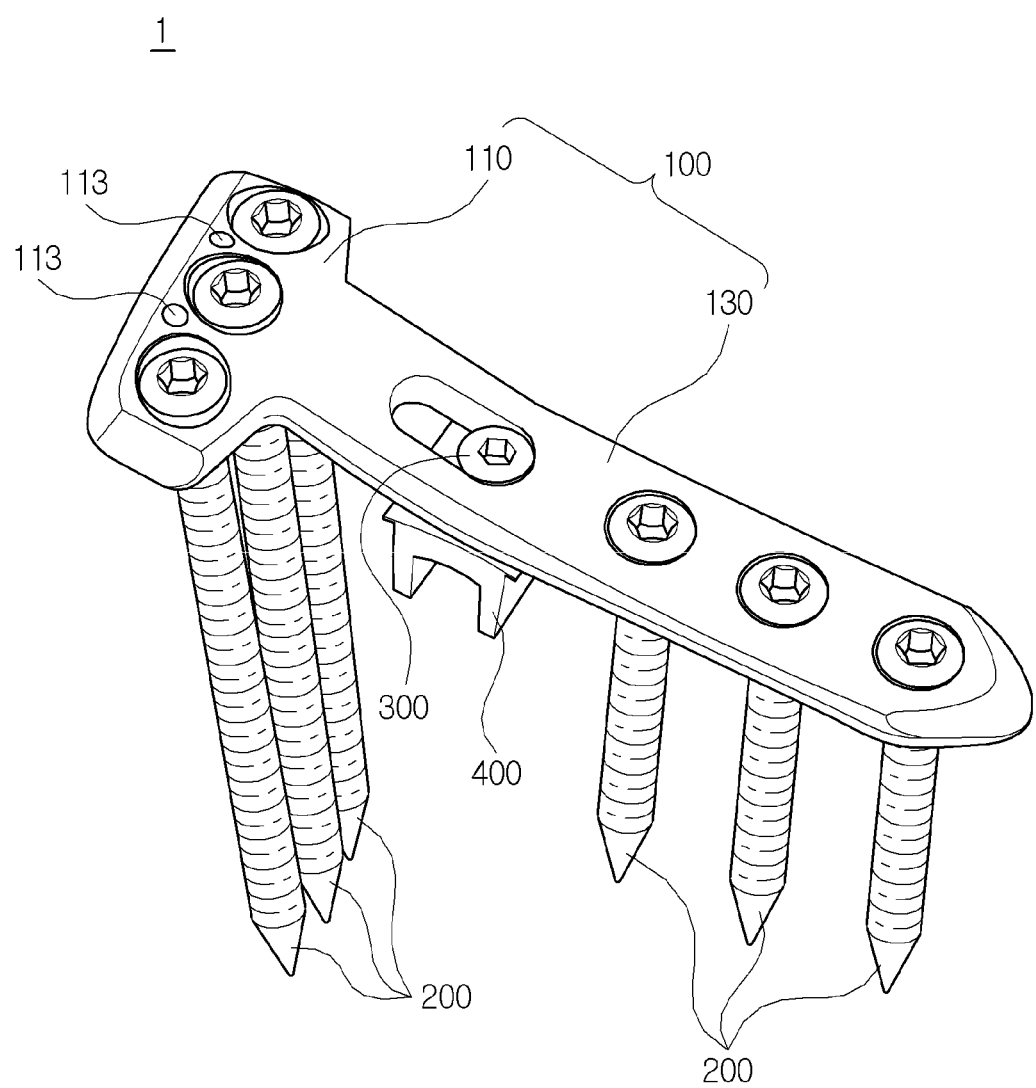
FIG. 4 is a perspective view illustrating the fixing tool for an open-wedge high tibial osteotomy according to the exemplary embodiment of the present invention.

Referring to FIG. 3, a cut-out portion 3 is formed due to a procedure of an open-wedge high tibial osteotomy that cuts a tibia 2. Therefore, the tibia 2 is divided into an upper tibia 2a and a lower tibia 2b, and an upper cut-out surface 4 and a lower cut-out surface 5 are formed due to the procedure.

A fixing tool 1 for an open-wedge high tibial osteotomy according to an exemplary embodiment of the present invention is closely fixed to the upper tibia 2a and the lower tibia 2b, which have been cut open due to the tibial osteotomy, thereby facilitating union of the upper tibia 2a and the lower tibia 2b after the procedure.

In addition, the fixing tool 1 for an open-wedge high tibial osteotomy supports a load applied to the tibia 2 until the union of the upper tibia 2a and the lower tibia 2b.

Referring to FIGS. 4 to 9, the fixing tool 1 for an open-wedge high tibial osteotomy may include a fixing plate 100, screws 200, a fixing screw 300, and a block 400.

Figure 5:
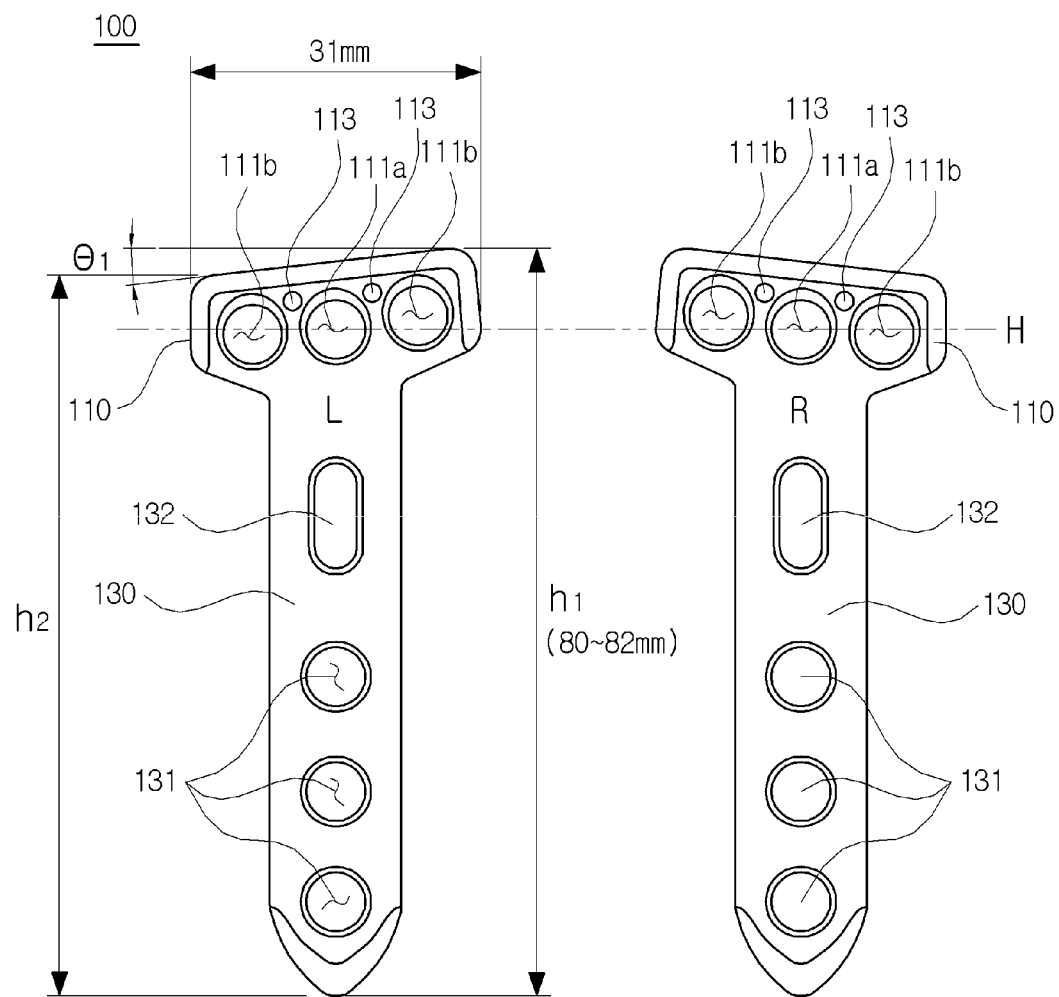
FIG. 5 is a view illustrating left and right fixing plates of the fixing tool for an open-wedge high tibial osteotomy according to the exemplary embodiment of the present invention.

As illustrated in FIG. 5, the fixing plate 100 may be classified into a left fixing plate L and a right fixing plate R, and the left fixing plate L and the right fixing plate R may be selectively used depending on the tibia 2 to be subjected to the procedure.

The fixing plate 100 may include a head portion 110 and an elongated plate 130.

The elongated plate 130 is formed to protrude from one side of the head portion 110, and thus the fixing plate 100 may be formed in a T shape as illustrated in FIG. 5.

Here, a thickness of the fixing plate 100 is about 3 mm, and an overall length of the fixing plate 100 is 80 to 82 mm, and a length of the head portion 110 in a longitudinal direction may be 31 mm.

A plurality of nut holes 111a, 111b, and 131 is formed in the head portion 110 and the elongated plate 130, respectively, so that the screws 200 may be coupled to the plurality of nut holes 111a, 111b, and 131.

Here, the nut holes 111a, 111b, and 131 are each formed to have a wide upper side and a narrow lower side by being cut away to have a tapered shape. Therefore, heads of the screws 200 are matched in shape with the nut holes 111a, 111*b*, and 131. Further, the heads of the screws 200 are supported by the nut holes 111*a*, 111*b*, and 131.

Figure 6:
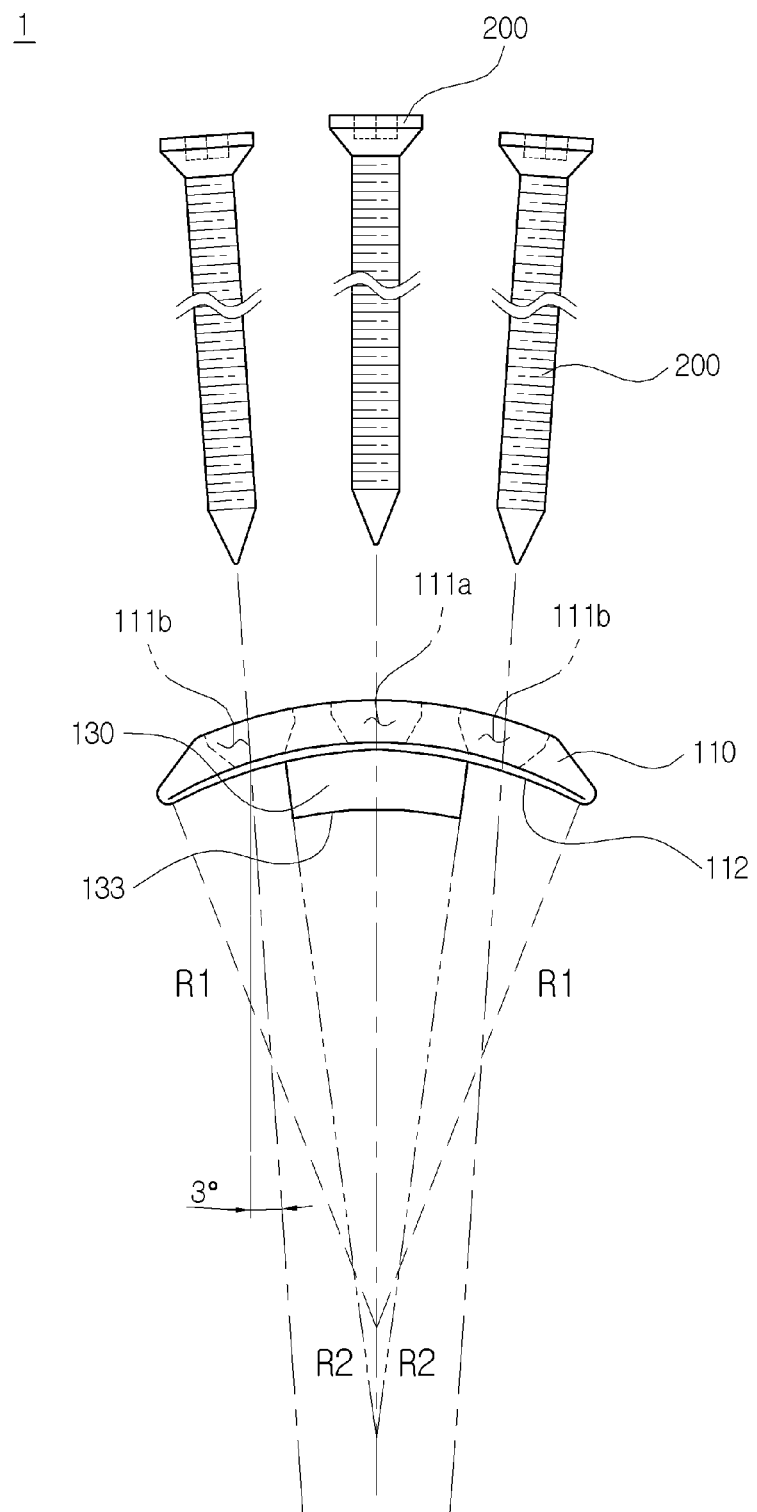
FIG. 6 is a view illustrating a head portion and a radius of curvature of an elongated plate of the fixing tool for an open-wedge high tibial osteotomy according to the exemplary embodiment of the present invention.

Referring to FIG. 6, the head portion 110 are curvedly formed to have a predetermined radius of curvature R1. In particular, a head close contact surface 112 of the head portion 110 is curvedly formed to have the predetermined radius of curvature R1 so that the head close contact surface 112 may be closely attached to one side of an outer surface of the upper tibia 2*a*.

Further, since the head close contact surface 112 of the head portion 110 is curvedly formed, the screw 200 installed in the nut hole 111*b* may be installed to be inclined toward a center of the radius of curvature R1 as illustrated in FIG. 6.

Of course, the screw 200 installed in the nut hole 111*b* may be installed to be inclined toward the center of the radius of curvature R1 as described above, but the present invention is not necessarily limited thereto, and an angle at which the screw 200 installed in the nut hole 111*b* is installed may be adjusted by adjusting an angle at which the nut hole 111*b* is formed.

Therefore, as illustrated in FIG. 6, in consideration of a separation interval between the screw 200 installed in the nut hole 111*a* and the screw 200 installed in the nut hole 111*b*, the screw 200 installed in the nut hole 111*b* may be installed to be inclined at about 2 to 4 degrees based on a central axis in the longitudinal direction of the screw 200 installed in the nut hole 111*a*, and may be installed to be inclined at about 3 degrees.

That is, the head screw 200 installed in the nut hole 111*b* is installed toward a centerline that connects a center of the head portion 110 and the center of the radius of curvature R1, and a tip of the head screw 200 installed in the nut hole 111*b* is installed to be spaced apart from the centerline.

Figure 7:
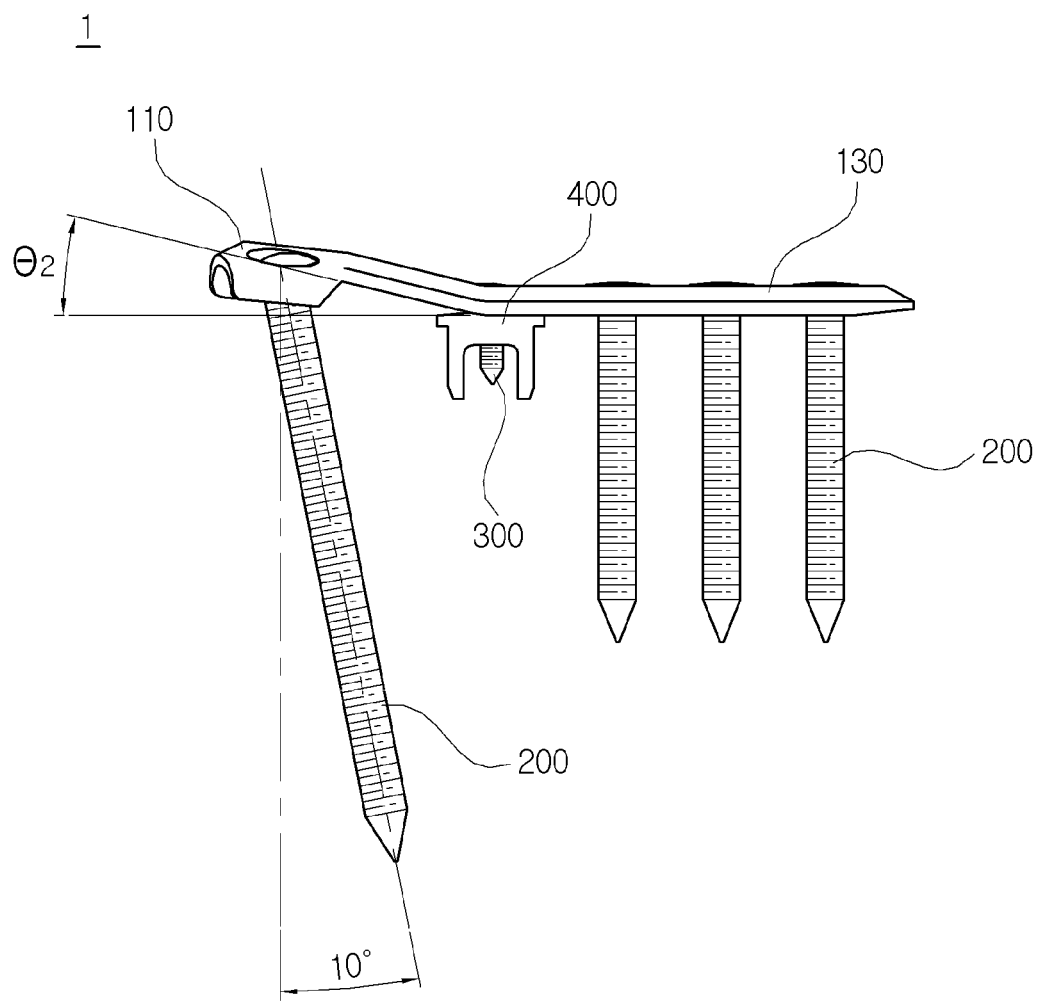
FIG. 7 is a side view of the fixing tool for an open-wedge high tibial osteotomy according to the exemplary embodiment of the present invention.
Figure 8:
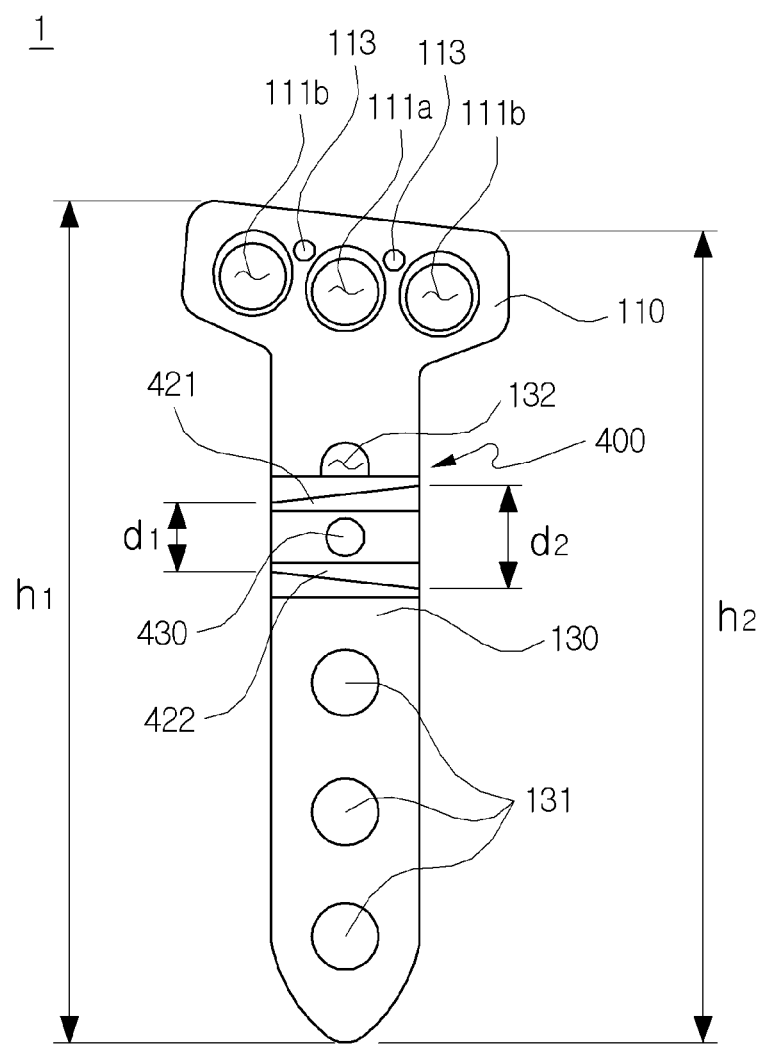
FIG. 8 is a view illustrating a block installed on the fixing plate of the fixing tool for an open-wedge high tibial osteotomy according to the exemplary embodiment of the present invention.
Figure 9:
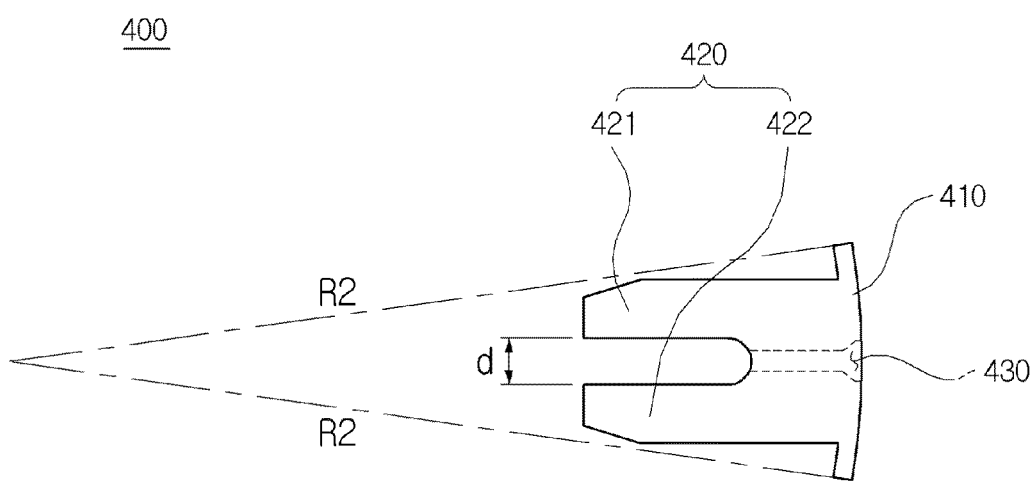
FIG. 9 is a side view illustrating the block of the fixing tool for an open-wedge high tibial osteotomy according to the exemplary embodiment of the present invention.

Meanwhile, as illustrated in FIG. 7, the nut holes 111*a* and 111*b* formed in the head portion 110 may be formed to have a gradient of 8 to 12 degrees in a direction toward the elongated plate 130. In particular, the nut holes 111*a* and 111*b* may be formed to have a gradient of 10 degrees.

Therefore, the screws 200 installed in the nut holes 111*a* and 111*b* formed in the head portion 110 are installed in the upper tibia 2*a* with a gradient of 10 degrees in the direction toward the elongated plate 130. Therefore, the plurality of screws 200 installed in the upper tibia 2*a* may easily cope with a load applied to the fixing tool 1 for an open-wedge high tibial osteotomy.

In addition, since the screws 200 installed in the nut holes 111*a* and 111*b* are fixedly installed in the upper tibia 2*a* with a gradient of 10 degrees in the direction toward the elongated plate 130, the screws 200 are not easily withdrawn from the upper tibia 2*a* by external force and the load.

Meanwhile, as illustrated in FIG. 5, the head portion 110 may be inclinedly formed to have an inclination angle $\theta 1$ based on an imaginary horizontal line H that transverses the center of the head portion 110. That is, an edge of the head portion 110, which is opposite to a portion connected to the elongated plate 130, may be inclinedly formed to have the inclination angle $\theta 1$.

Here, the inclination angle $\theta 1$ may be 5 to 7 degrees.

Therefore, a height h1 from an end of the elongated plate 130 to one side of a side edge of the head portion 110 is greater than a height h2 of the other side of the head portion 110.

Since the height h1 of one side of the side edge is greater than the height h2 of the other side, a contact area between the tibia 2 and the side edge h1 of the fixing tool 1 for an open-wedge high tibial osteotomy is increased. Therefore, the procedure is carried out such that the side edge h1 is positioned at a front side (a patella side) of the tibia 2, and as a result, it is possible to more easily cope with a load applied to the front side of the tibia 2. In addition, it is also possible to easily cope with external force applied from the front side of the tibia 2.

The head portion 110 may further include at least two guide holes 113 formed such that guide pins (not illustrated) are installed in at least two guide holes 113.

The guide pins are installed in the upper tibia 2*a* while penetrating the guide holes 113 before the screws 200 are installed, and as a result, the fixing plate 100 is temporarily fixed.

Therefore, the guide pin prevents the fixing plate 100 from being moved when the screws 200 are installed in the fixing plate 100. In addition, it is not necessary for a practitioner to hold the fixing plate 100 in order to install the screws 200.

The guide pins are removed after the screws 200 are installed.

Hereinafter, the elongated plate 130 will be described with reference to FIGS. 5 to 7.

As illustrated in FIG. 6, the elongated plate 130 may be curvedly formed in a width direction.

The elongated plate 130 is curvedly formed to have a predetermined radius of curvature R2. In particular, a plate close contact surface 133 of the elongated plate 130 is curvedly formed to have the predetermined radius of curvature R2 so that the plate close contact surface 133 may be closely attached to one side of an outer surface of the lower tibia 2*b*.

The radius of curvature R2 of the plate close contact surface 133 may be different from the radius of curvature R1 of the head close contact surface 112. In particular, the radius of curvature R2 of the plate close contact surface 133 may be greater than the radius of curvature R1 of the head close contact surface 112.

That is, because the outer surface of the lower tibia 2*b* may be formed as a flat outer surface unlike the upper tibia 2*a*, the radius of curvature R2 of the plate close contact surface 133 may be greater than the radius of curvature R1 of the head close contact surface 112 in accordance with a position of the tibia 2 to be subjected to the tibial osteotomy.

Referring to FIG. 7, a portion of the elongated plate 130 connected with the head portion 110 may be bent to have a bending angle $\theta 2$. Here, the bending angle $\theta 2$ may be 13 to 16 degrees, and particularly, 15 degrees.

Because an outer diameter of the upper tibia 2*a* is greater than an outer diameter of the lower tibia 2*b*, the elongated plate 130, which is bent from the head portion 110 with the bending angle $\theta 2$, is easily closely attached to the lower tibia 2*b*.

Meanwhile, the elongated plate 130 protrudes from one side of the head portion 110, and may have the upper nut hole 131*a*, the lower nut holes 131*b*, and a long hole 132.

The long hole 132 is formed to be elongated in a longitudinal direction of the elongated plate 130.

Further, the block 400 is detachably installed in the long hole 132 by using the fixing screw 300.

In addition, the block 400 is moved along the long hole 132 and then fixedly installed in the elongated plate 130 by the fixing screw 300 so that the block 400 is installed to correspond to a position of the cut-out portion 3.

Referring to FIGS. 8 to 12, the block 400 may include an upper plate 410, a pair of support protrusions 420 which is installed to protrude from one side of the upper plate 410 so as to be spaced apart from each other, and a coupling hole 430 which is formed such that the fixing screw 300 is coupled into the coupling hole 430. Here, the pair of support protrusions 420 may include an upper support protrusion 421 and a lower support protrusion 422.

The block 400 is installed in the cut-out portion 3, and prevents the upper cut-out surface 4 and the lower cut-out surface 5 from approaching each other by a load applied to the tibia 2.

One side surface of the upper plate 410 is curvedly formed to have the predetermined radius of curvature R2. Therefore, the block 400 may be installed to be closely attached to the plate close contact surface 133 of the elongated plate 130.

Figure 10:
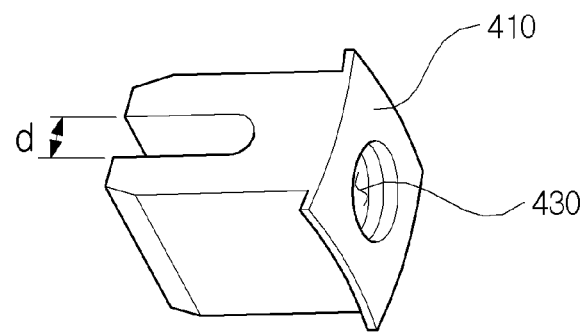
FIG. 10 is a view illustrating various exemplary embodiments of the block of the fixing tool for an open-wedge high tibial osteotomy according to the exemplary embodiment of the present invention.
Figure 10:
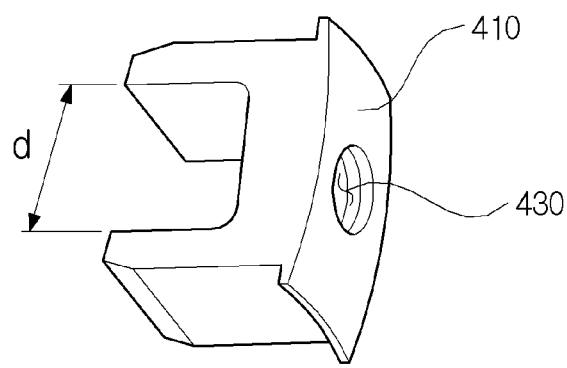
Figure 10:
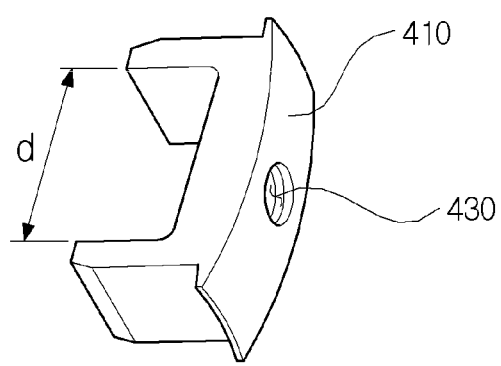

The upper support protrusion 421 and the lower support protrusion 422 are formed to be spaced apart from each other at a separation distance d. Here, as illustrated in FIG. 10, the separation distance d may be set to be various intervals of 6 to 16 mm. Therefore, a variety of blocks 400 may be selected in accordance with a size of the cut-out portion 3, and then installed into the elongated plate 130.

Figure 11:
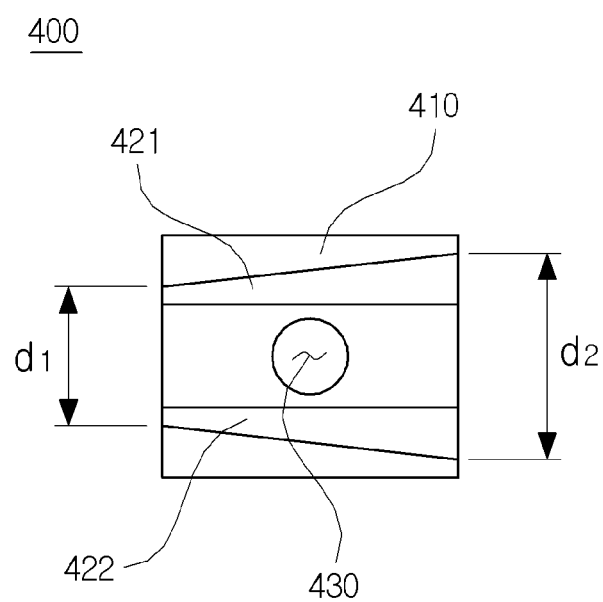
FIG. 11 is a bottom plan view illustrating the block of the fixing tool for an open-wedge high tibial osteotomy according to the exemplary embodiment of the present invention.

At least one of the upper support protrusion 421 and the lower support protrusion 422 may be formed to be inclined in a width direction. In particular, as illustrated in FIG. 11, a ratio between a length $d_1$ of one side from the lower support protrusion 422 to the upper support protrusion 421 and a length $d_2$ of the other side may be 2:3.

Further, the block 400 may be installed in the elongated plate 130 such that the d1 is positioned at a side adjacent to a patella.

Figure 12A:
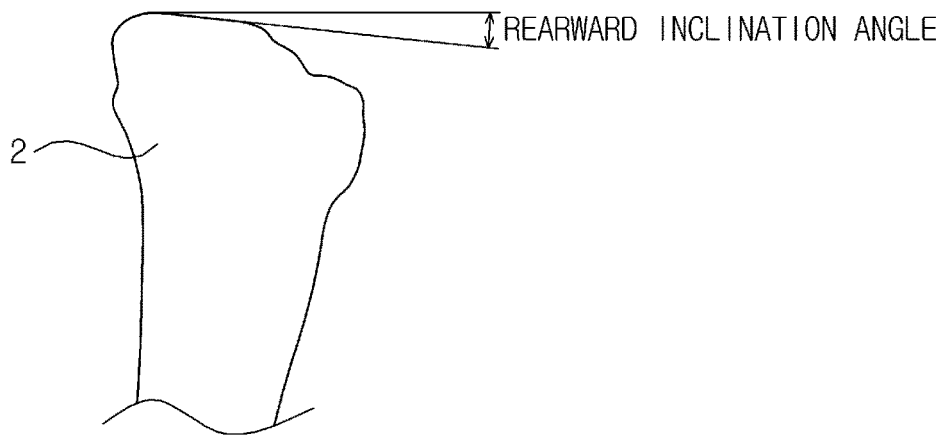
FIG. 12A, FIG. 12B, and FIG. 12C are views illustrating the block installed in a cut-out portion which has been cut open due to an open-wedge high tibial osteotomy.
Figure 12B:
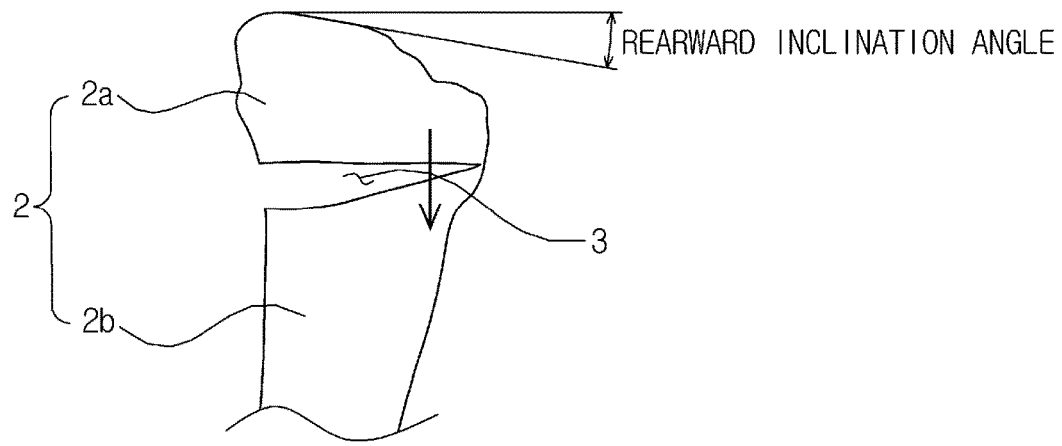

As illustrated in FIG. 12A, the tibia 2 has a rearward inclination angle, and as illustrated in FIG. 12B, the rearward inclination angle is increased by the cut-out portion 3 because of the procedure of the open-wedge tibial osteotomy.

Figure 12C:
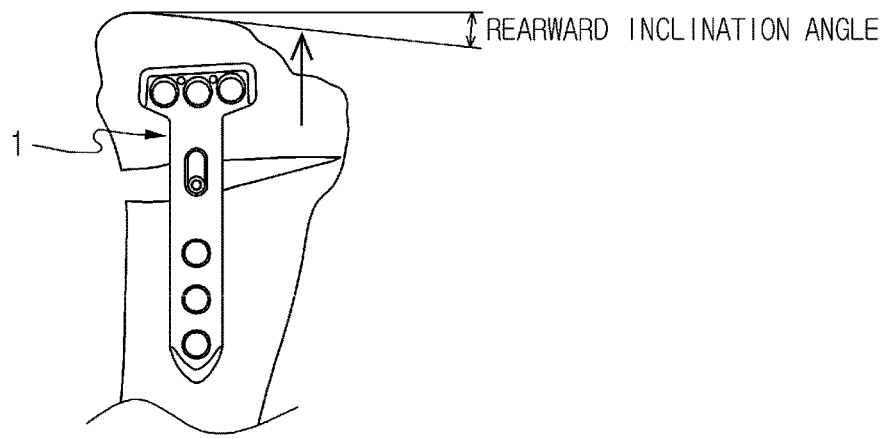

However, as illustrated in FIG. 12C, since the block 400 is installed in the cut-out portion 3, the rearward inclination angle of the tibia 2 may be maintained.

Further, tips of the upper support protrusion 421 and the lower support protrusion 422 are formed in a pointed shape so that the upper support protrusion 421 and the lower support protrusion 422 are easily installed, and the tips may be chamfered.

Collectively, the fixing tool 1 for an open-wedge high tibial osteotomy is closely fixed to the tibia 2, which has been cut open due to the high tibial osteotomy, and supports a load applied to the tibia 2, thereby allowing bone growth into the cut-out portion 3 and enabling a quick union.

The various exemplary embodiments according to the present invention may of course solve a variety of technical problems other than the contents mentioned in the present specification in the related technical field as well as the corresponding technical field.

As the foregoing, the present invention has been described with reference to the exemplary embodiments. However, those skilled in the art will clearly understand that the present invention may be embodied in any other modified form without departing from the basic technical spirit of the present invention. Thus, it should be appreciated that the disclosed exemplary embodiments are intended to be illustrative, not restrictive. That is, it should be construed that the true technical scope of the present invention is determined by the appended claims, and all differences within the equivalent scope thereto are included in the scope of the present invention.

The invention claimed is:

1. A fixing tool for an open-wedge high tibial osteotomy, which is adapted to be installed on a tibia cut open due to an open-wedge tibial osteotomy, the fixing tool comprising:

a fixing plate which includes a head portion that has a plurality of nut holes, and an elongated plate portion that has a plurality of nut holes and a long hole and is formed to protrude from one side of the head portion;
screws which are coupled to the nut holes; and
a block which is detachably installed by the long hole by using a fixing screw, the block having two tapered protrusions protruding from a body of the block,
wherein the tapered protrusions are tapered along a distal facing surface of the protrusions so that a first side of the distal facing surface is thicker than a second side of the distal facing surface.

2. The fixing tool of claim 1, wherein the head portion has a predetermined curvature.

3. The fixing tool of claim 2, wherein the screws installed in the head portion are inclined toward a center of the curvature.

4. The fixing tool of claim 2, wherein tips of the screws, which are installed toward a centerline that connects a center of the head portion and a center of the curvature, and installed at opposing sides of the center of the head portion, are spaced apart from the centerline.

5. The fixing tool of claim 1, wherein the nut hole formed in the head portion is inclinedly formed to have a gradient of 8 to 12 degrees in a direction toward the elongated plate portion.

6. The fixing tool of claim 1, wherein an opposite side of the head portion is inclined at an inclination angle with respect to a longitudinal axis of the elongated plate portion.

7. The fixing tool of claim 6, wherein the inclination angle is 5 to 7 degrees.

8. The fixing tool of claim 1, wherein a part of the elongated plate portion connected with the head portion is bent to have a bending angle.

9. The fixing tool of claim 8, wherein the bending angle is 13 to 16 degrees.

10. The fixing tool of claim 1, wherein a width of the elongated plate portion has a predetermined curvature.

11. The fixing tool of claim 1, wherein the block includes an upper plate; and the protrusions protrude from a side surface of the upper plate.

12. The fixing tool of claim 11, wherein the other side surface of the upper plate is a curved surface having a predetermined curvature.

13. The fixing tool of claim 12, wherein the elongated plate portion is curved in a width direction to have a predetermined curvature, and the curvature of the elongated plate portion and the curvature of the upper plate are equal to each other.

14. The fixing tool of claim 1, wherein a ratio between a distance between opposing corners of the protrusions on the second side to a distance between opposing corners of the protrusions on the first side is 2:3.

15. The fixing tool of claim 1, wherein the head portion includes at least two guide holes formed such that guide pins are installed in at least two guide holes.

16. The fixing tool of claim 1, wherein the protrusions are symmetric about a midpoint of a space between the protrusions.

17. The fixing tool of claim 16, wherein the block comprises a hole for the fixing screw in the space between the protrusions.

18. The fixing tool of claim 1, wherein outer faces of the protrusions are adapted to support exposed surfaces of the tibia.

* * * * *